(12) United States Patent
LaCroix et al.

(10) Patent No.: US 11,009,450 B2
(45) Date of Patent: May 18, 2021

(54) SYSTEMS AND METHODS FOR QUALITY TESTING OF ASPHALT BY PREDICTING AN INDIRECT TENSILE STRENGTH RATIO OF THE ASPHALT SAMPLE BASED ON THE BINDER LOSS VALUE

(71) Applicant: InstroTek, Inc., Raleigh, NC (US)

(72) Inventors: Andrew LaCroix, Raleigh, NC (US); Lawrence James, Raleigh, NC (US); Ali Regimand, Raleigh, NC (US); Dirk Steckmann, Raleigh, NC (US); Ethan Steckmann, Durham, NC (US)

(73) Assignee: InstroTek, Inc., Raleigh, NC (US)

( * ) Notice: Subject to any disclaimer, the term of this patent is extended or adjusted under 35 U.S.C. 154(b) by 0 days.

(21) Appl. No.: 16/729,617

(22) Filed: Dec. 30, 2019

(65) Prior Publication Data

US 2020/0209149 A1    Jul. 2, 2020

Related U.S. Application Data

(60) Provisional application No. 62/786,674, filed on Dec. 31, 2018.

(51) Int. Cl.
| | | |
|---|---|---|
| *G01N 21/25* | (2006.01) | |
| *G01N 1/44* | (2006.01) | |
| *G01N 21/27* | (2006.01) | |

(52) U.S. Cl.
CPC ............ *G01N 21/251* (2013.01); *G01N 1/44* (2013.01); *G01N 21/274* (2013.01); *G01N 2201/061* (2013.01)

(58) Field of Classification Search
CPC ...... G01N 21/251; G01N 1/44; G01N 21/274; G01N 2201/061; G01N 33/42; G01N 2201/062; G01N 2201/1211; G01N 21/84
See application file for complete search history.

(56) References Cited

U.S. PATENT DOCUMENTS

| | | | | |
|---|---|---|---|---|
| 4,700,223 | A * | 10/1987 | Shoutaro | G01C 7/04 348/148 |
| 2004/0121473 | A1* | 6/2004 | He | G01N 33/42 436/61 |
| 2008/0184785 | A1* | 8/2008 | Wee | G01B 11/306 73/104 |
| 2008/0262780 | A1* | 10/2008 | Bienvenu | E02D 1/00 702/127 |
| 2009/0314090 | A1* | 12/2009 | Troxler | G01N 33/24 73/623 |
| 2012/0227475 | A1* | 9/2012 | Troxler | G01N 9/02 73/73 |
| 2012/0304763 | A1* | 12/2012 | Troxler | G01B 11/24 73/32 R |

* cited by examiner

*Primary Examiner* — Michael P LaPage
(74) *Attorney, Agent, or Firm* — Myers Bigel, P.A.

(57) ABSTRACT

A method for quality testing asphalt includes: directing light from a light source to at least one surface of asphalt; detecting light reflected or refracted from the at least one surface of the asphalt using a light detector; and assigning a number indicating the quality of the asphalt in response to detecting light reflected or refracted from the at least one surface of the asphalt.

14 Claims, 8 Drawing Sheets

SYSTEMS AND METHODS FOR QUALITY TESTING OF ASPHALT BY PREDICTING AN INDIRECT TENSILE STRENGTH RATIO OF THE ASPHALT SAMPLE BASED ON THE BINDER LOSS VALUE

RELATED APPLICATIONS

This application claims priority from U.S. Provisional Application No. 62/786,674, filed Dec. 31, 2018, the disclosure of which is hereby incorporated by reference herein in its entirety.

BACKGROUND

During asphalt or bituminous mixture design, one of the primary concerns is the adhesion strength (quality) between the asphalt binder and the aggregate. If these components have poor adhesion strength, the mixture is likely to perform poorly when placed on an asphalt pavement. Many tests have been developed over the years to determine the adhesion strength between the asphalt binder and aggregate. One of these tests is the asphalt mixture boil test, as described in ASTM D3625. The boil test is used by highway agencies and material testing labs to quickly determine adhesion or compatibility of the mixture by visually observing a change in color of asphalt. The test procedure involves boiling an approximately 250 g sample of mixture in distilled water for 10 minutes or more and then estimating the amount of binder that is stripped from the aggregate based on visual observation. If the asphalt binder and aggregate have low quality, the asphalt binder will tend to debond from the aggregate and the aggregate will be exposed, which is quantified as percentage of stripped area or percent loss. The challenge with visual quantification of the compatibility is that each person evaluates and quantifies the loss differently. The current invention produces a quantitative and reproducible number representative of the percent stripped.

SUMMARY

Some embodiments of the present invention are directed to a method for quality testing asphalt. The method includes: directing light from a light source to at least one surface of asphalt; detecting light reflected or refracted from the at least one surface of the asphalt using a light detector; and assigning a number indicating the quality of the asphalt in response to detecting light reflected or refracted from the at least one surface of the asphalt.

In some embodiments, the asphalt is on a road.

In some embodiments, the asphalt is an asphalt sample. The method may further include: providing an asphalt quality system including a measurement sensor including the light source and the light detector and a controller in communication with the measurement sensor; preparing the asphalt sample; and receiving the asphalt sample in a sample container or open ended mold. Assigning a number indicating the quality of the asphalt may include, using the controller, determining a color index of the asphalt sample in response to detecting light reflected or refracted from the at least one surface of the asphalt sample.

In some embodiments, the method includes: using the controller, determining a binder loss value of the asphalt sample based on the determined color index; and displaying the color index of the asphalt sample and/or the binder loss value of the asphalt sample on a display of the controller.

In some embodiments, the method includes, using the controller, predicting an indirect tensile strength ratio (TSR) of the asphalt sample based on the binder loss value.

In some embodiments, the asphalt quality system further includes a testing cabinet. The method may further include, before directing light from the light source to the at least one surface of the asphalt sample: loading the sample container or open ended mold with the asphalt sample therein in the testing chamber; and receiving the measurement sensor in the testing chamber.

In some embodiments, receiving the asphalt sample in a sample container or open ended mold includes receiving the asphalt sample in a sample container, wherein the measurement sensor includes a sensor housing holding a light source and a light detector and a light tube extending away from the sensor housing, and wherein receiving the measurement sensor in the testing cabinet includes receiving at least a portion of the light tube in the sample container.

In some embodiments, preparing the asphalt sample includes boiling the asphalt sample and drying the boiled asphalt sample. The asphalt quality system may further include a drying kit comprising a dryer, a drying pan, and a drying stand and/or a stand clamp coupling the dryer and the drying pan. Drying the boiled asphalt sample may include: receiving the boiled asphalt sample in the drying pan; blowing air on the boiled asphalt sample using the dryer; and optionally tilting the drying pan such that water drains away from the boiled asphalt sample.

In some embodiments, the method includes: using the asphalt quality system, determining a color index of an unboiled asphalt sample; using the asphalt quality system, determining a color index of a raw aggregate; and using the controller, determining a calibration curve based on the color index of the unboiled asphalt sample and the color index of the raw aggregate. Determining the color index of the asphalt sample may include using the calibration curve.

In some embodiments, the asphalt quality system further includes a standard holder configured to hold a standard comprising a reference material. The method may further include: receiving the measurement sensor in the standard holder; directing light from the light source to the standard; detecting reflected light from the standard using the light detector; and using the controller, normalizing the effect of normal temperature changes in the laboratory to the sample by incorporating the response to detecting reflected light from the standard.

In some embodiments, receiving the asphalt sample in a sample container or open ended mold includes receiving the asphalt sample in a sample container. The method may further include tamping the asphalt sample in the sample container such that the asphalt sample is at a predetermined height in the sample container.

In some embodiments, receiving the asphalt sample in a sample container or open ended mold includes receiving the asphalt sample in an open ended mold. The at least one surface of the asphalt sample may be a first surface of the asphalt sample, and the color index may be a first color index. The method may further include: flipping the asphalt sample; directing light from the light source to a second surface of the asphalt sample that is opposite the first surface of the asphalt sample; detecting light reflected from the second surface of the asphalt sample using the light detector; using the controller, determining a second color index of the asphalt sample in response to detecting light reflected from the second surface of the asphalt sample; and optionally, using the controller, comparing the first and second color indexes of the asphalt sample.

In some embodiments, the asphalt quality system further includes a testing cabinet. The method may further include: removing the open ended mold with the asphalt sample therein from the testing cabinet before flipping the asphalt sample; and loading the open ended mold with the asphalt sample therein in the testing cabinet after flipping the asphalt sample.

Some other embodiments of the present invention are directed to an asphalt quality testing system. The system includes: a measurement sensor including a sensor housing holding a light source and a light detector and a light tube extending away from the sensor housing; and a controller in communication with the measurement sensor, wherein the controller is configured to determine a color index of the asphalt sample based on measurements of asphalt from the measurement sensor.

In some embodiments, the asphalt is on a road.

In some embodiments, the controller is configured to output a binder loss index value based on the determined color index.

In some embodiments, the controller is configured to predict an indirect tensile strength ratio (TSR) of the asphalt based on the determined binder loss index value.

In some embodiments, the asphalt is an asphalt sample. The measurement sensor may be configured to direct light to a textured surface of the asphalt sample a plurality of times at different heights and positions and to detect reflected and/or refracted light from the textured surface to generate the measurements of the asphalt sample.

In some embodiments: the measurements of the asphalt sample from the measurement sensor are first measurements of the asphalt sample from the measurement sensor; the color index of the asphalt sample is a first color index of the asphalt sample; the measurement sensor is configured to direct light to a textured first surface of the asphalt sample to detect reflected and/or refracted light from the textured first surface to generate the first measurements of the asphalt sample; the measurement sensor is configured to direct light to a textured second surface of the asphalt sample to detect reflected and/or refracted light from the textured second surface to generate second measurements of the asphalt sample; the controller is configured to determine a second color index of the asphalt sample based on the second measurements of the asphalt sample from the measurement sensor; and/or the controller is optionally configured to compare the first and second color indexes of the asphalt sample.

In some embodiments, the controller is configured to generate a calibration curve based on a color index of an unboiled asphalt sample and a color index of a raw aggregate, and to determine the color index of the asphalt sample using the calibration curve.

In some embodiments, the system further includes a standard holder configured to hold a standard comprising a reference material, the standard holder including an upper panel with an opening defined therein. The measurement sensor may be configured to be received in the standard holder in a temperature test position with the sensor housing on the upper panel of the standard holder and the light tube adjacent and/or abutting the standard. The controller may be configured to normalize the effect of temperature using measurements of the standard from the measurement sensor.

In some embodiments, the system further includes a sample drying kit including: a dryer; a drying pan; a drying stand and/or a stand clamp coupling the dryer and the drying pan; and the drying stand and/or the stand clamp are optionally configured to tilt the drying stand to allow water to drain from a wet asphalt mixture.

In some embodiments, the system further includes a sample preparation kit comprising: a sample container configured to receive the asphalt sample therein; a stirring device configured to mix coarse and fine particles in the asphalt sample in the sample container; and a tamp configured to compress the asphalt sample at a predetermined height in the sample container.

In some embodiments, the system further includes a testing cabinet configured to hold the asphalt sample, the testing cabinet including an opening defined in an upper surface thereof. The measurement sensor may be configured to be received in the testing cabinet in a test position with the sensor housing on the upper surface of the testing cabinet and the light tube received in the opening and optionally spaced apart from the asphalt sample. The sample may be held in a sample container, and the testing cabinet may be configured to hold the sample container with the asphalt sample therein, and, in the test position, the light tube may be received in the sample container.

In some embodiments, the system further includes a sample preparation kit including: an open ended mold configured to receive the asphalt sample therein; a mold extension configured to be stacked on a perimeter of the open ended mold; a tamp configured to be received through the mold extension and configured to compact the asphalt sample in the open ended mold; and optionally a first plate configured to receive a first surface of the asphalt sample thereon and a second plate configured to receive an opposite second surface of the asphalt sample thereon.

Further features, advantages and details of the present invention will be appreciated by those of ordinary skill in the art from a reading of the figures and the detailed description of the preferred embodiments that follow, such description being merely illustrative of the present invention.

DETAILED DESCRIPTION

The present invention now will be described more fully hereinafter with reference to the accompanying drawings, in which illustrative embodiments of the invention are shown. In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Like numbers refer to like elements throughout. As used herein the term "and/or" includes any and all combinations of one or more of the associated listed items.

In addition, spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

Well-known functions or constructions may not be described in detail for brevity and/or clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises," "includes," "comprising," and/or "including," when used in this specification, specify the presence of stated features, integers, steps, operations, elements, and/or components, but do not preclude the presence or addition of one or more other features, integers, steps, operations, elements, components, and/or groups thereof.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The term "automatically" means that the operation is substantially, and may be entirely, carried out without human or manual control, direction and/or input, and can be programmatically directed or carried out.

The term "programmatically" refers to operations directed and/or primarily carried out electronically by computer program modules, code and/or instructions.

The concept of colorimetry may be applied to the boil test to develop a repeatable quantitative measurement. The change in the color index ($L^*$) from an unboiled (original) sample to a boiled sample may be calculated to quantify the amount of color loss, which is correlated to quality loss of the mixture. Furthermore, since many of the mixtures currently use additives (anti-strip additives) to help strengthen the bond between aggregates and asphalt binder, the change in color index can also be used to evaluate different anti-strip additives to determine the optimum dosage rate during asphalt mixture design. This is valuable because anti-strip is a relatively expensive component of asphalt mixture, so optimizing the dosage without sacrificing the performance can provide a cost advantage in the competitive binder environment. Another benefit of using the color index is its good correlation to the indirect tensile strength ratio (TSR) determined following the AASHTO T 283 and ASTM D4867 test methods for determination of moisture damage susceptibility. This correlation allows the prediction of the TSR value, which is one of the most popular tests performed in the pavement industry during design, quality control and quality assurance. The time savings using the color index method is significant because the AASHTO T 283 and ASTM D4867 procedures can take up to 7 days to complete and to get the results, while the boil test and color index determination can take less than 60 minutes. Because of the time savings, the boil test could be used as a quality control procedure to ensure that required changes in the production process during asphalt mixture production do not result in adhesion failure in the mixtures, and thereby poor pavement quality.

This method can be applied to many of the tests in the industry where the condition of the material or pavement can be assessed by change in the texture or color of the material. For example, an application of this device is measuring the wear on a pavement surface. For financial reasons, many roads are rehabilitated with a bituminous surface treatment. Knowing the % loss of the treatment over time is helpful in determining the condition of the road and subsequent treatment planning. The color index can be used in this case on the roadway to determine percent treatment loss from the surface of the pavement. The same measurements can also be used to predict aging of the material on the pavement. As materials age over time, the color can be used to predict remaining life or condition of asphalt in the lab and/or the road surface. Furthermore, this method can be used to determine set point period (break) for tack coat used prior to application of new asphalt pavement jobs or for chip seal application.

Given the benefits of using a device, such as a colorimeter, to quantify the color change of an asphalt mixture, which can be used to detect adhesion strength of asphalt mixtures (including hot-mix, warm-mix, chip seal, slurry seal, in-place and plant-produced recycled asphalt mixture products), as well as additional uses such as surface wear of asphalt pavements, aging of asphalt mixtures, and asphalt content of asphalt mixtures, the following innovative advances have been made to allow accurate and repeatable application of color index measurement for material testing: 1) improve the repeatability of the measurement of an asphalt mixture sample by reducing material surface texture effect from asphalt samples, 2) develop a calibration that relates to the actual performance called the % loss,
3) develop a method to estimate the probability that a mixture has a low, medium, or high probability of failure due to compatibility between the asphalt binder and aggregate by quantifying the degree of loss, and
4) eliminate temperature that could significantly affect the color index. These developments are combined to form the systems and methods for quality testing of asphalt using color change or colorimeters according to embodiments of the present invention (e.g., asphalt compatibility or quality tester (ACT)).

The biggest challenge with repeatable measurements of asphalt mixtures is the variability of the mixtures themselves. A given mixture will contain a variety of different aggregate sizes ranging from microns to tens of millimeters and a variety of aggregate sources, such as granite, limestone, sand, and mineral filler. Each source and size may have a different compatibility with the binder of the mixture. Therefore, the procedure for preparing and measuring the sample should allow the ACT to take several snapshots of the mixture to capture the coarse and fine fractions of the mixture. Another feature of the sample preparation procedure is the process should be as quick as possible. Since the mixture has to be boiled before testing, the sample will need to be dried before testing, otherwise the color changes as the water evaporates from the sample. Therefore, a specimen preparation procedure has been developed for the ACT. A summary of the procedure is the asphalt mixture sample is boiled, then the sample is dried, next the sample is prepared inside the sample container, and finally the adhesion quality is measured (details are provided below).

The response of the ACT may be calibrated to a colorimeter to obtain L* (color index) and then calibrated to measure the % loss on a particular aggregate mix. Or the ACT may be used without calibration to a colorimeter using the raw number to obtain the % loss calibration of a specific mixture.

A key component of the ACT procedure is getting a consistent surface of the mixture. Loose asphalt mixture can have a very rough textured surface. The surface appears darker with more texture because more light is trapped in the low spots of the surface instead of being reflected back to the sensor. Another method of reducing the variability of measurements is measuring the same surface at different heights. By measuring the surface at different heights and then calculating the difference or ratio, the surface effect, which is in both measurements, cancels out and the resulting value is the effect of the color, not texture. Based on this discovery, the ACT can be used to detect changes in texture as well as changes in compatibility. Another development of the ACT is a procedure to determine % loss. This development translates the color measurement into a physical value that asphalt users and engineers are familiar with. The Ministry of Ontario Static Immersion Test (LS-285) provides a method to quantify the % loss by using reference cards with different areas of white space on a black background, which is defined as the % loss. The challenge with this method is the 2D image of the reference card has to be converted to a 3D sample that is affected by the texture. Due to the variety of aggregates mentioned earlier, the ACT device has to be calibrated. The calibration entails measuring the color index of an unboiled asphalt mixture sample to represent 0% loss. Then, a sample of the aggregate gradation, which represents 100% loss, is measured. From these two points, a linear relationship can be calculated that represents the % loss for that mixture.

Development of Calibration Procedure

The ACT measures light reflected from the surface of the asphalt mixture. As the surface of an asphalt mixture strips, the amount of reflected light increases, which increases the output (referred to as count) of the light sensor. The index for the change in the color is defined as the % Loss or the percentage of asphalt binder removed from the surface. The scale could also be the reverse relationship of 100%-% Loss, which could be called % Retain or % Coated. An increase in reflected light represents an increase in the % Loss. The scale of the % Loss is based on the idea that an unboiled asphalt mixture represents 0% Loss, while completely bare aggregates represent 100% Loss.

Figure 5:
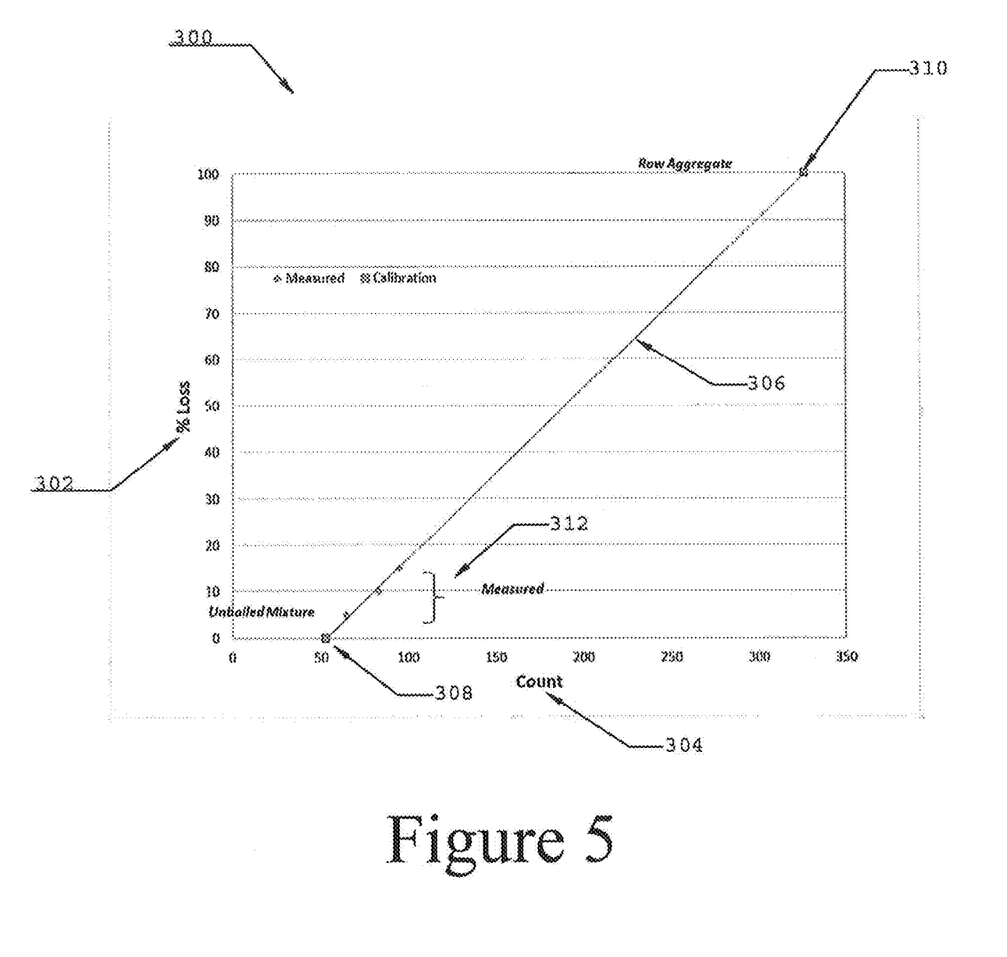
FIG. 5 is a graph illustrating proof of calibration concept according to some embodiments of the present invention.

In FIG. 5, the % Loss scale is shown for a given mixture and aggregate. The line was calibrated with the points at 0 and 100%. Then, samples with different percentages based of bare aggregate were used to simulate different quantities of loss. Measured counts for samples with 5, 10, and 15% bare aggregates match the trend of the calibration line.

Another development helpful to practitioners is a method to determine if the mixture is good, marginal, or bad and provide a statistical confidence of the result. In many adhesion tests, it is easy to identify good and bad performing mixtures. Marginal mixtures are more difficult to identify. To develop this scale, testing to determine the standard deviation of different mixtures is performed. Then, a limit is determined between the good and bad mixtures based on experience. The mixtures that are within a specified interval within the normal distribution of this limit are considered marginal mixtures.

Another development is a procedure to correct for the temperature effect on measurement readings. The ACT uses a light source such as one or more LEDs to illuminate the sample and a light sensor to measure the light reflected from the asphalt mixture. Both the intensity of the light source and the sensitivity of the light sensor can be affected by temperature. As the temperature increases, the light output and corresponding sensor measurements change proportionally. The effect can be removed by a ratio method because the temperature effect is present in two different measurements, which cancel out in the ratio. Examples of the ratio method include the method of normalizing the current measurement of a reference material to the measurement made during calibration or the method of ratioing two heights when accounting for texture. A reference material is supplied with the ACT for daily measurements to accommodate changes in temperature of the ACT. The reference measurement also provides users a method to check that the unit is operating properly. The check consists of comparing the current measurement to the measurement results obtained during calibration to see if the values are within a prescribed limit.

Figure 7:
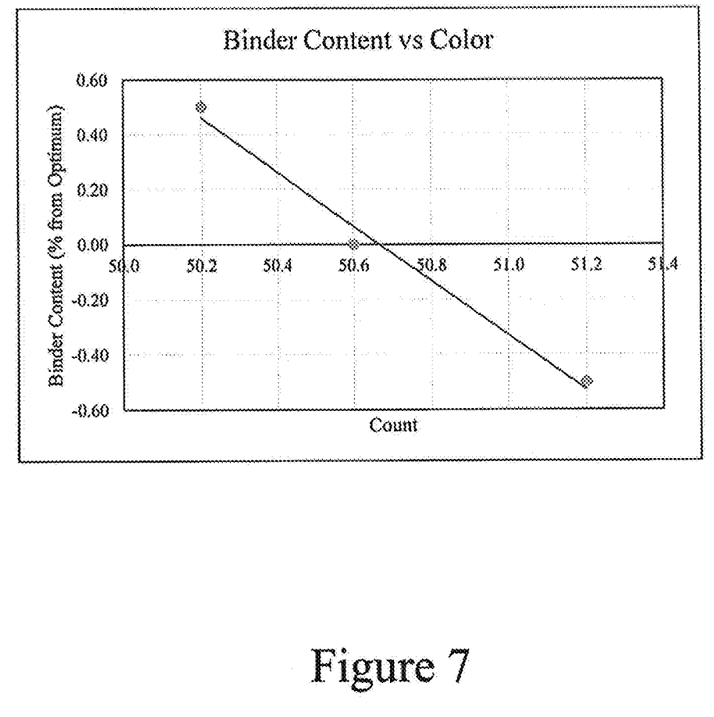
FIG. 7 is a graph illustrating the measurement of binder content using the system of FIG. 1.

Another development is a procedure to predict the asphalt content of a specific asphalt mixture. Currently, two methods are commonly used to measure the asphalt content of asphalt mixtures: binder extraction using solvents and an asphalt ignition oven (muffle furnace) to burn off the asphalt binder. Both these methods require special safety procedures to perform the measurement such as proper handling of solvents in binder extraction or protection from extreme heat in the asphalt ignition method. An alternative method is to measure the asphalt content using the ACT. As mentioned earlier, the ACT measures the amount of light reflected by the asphalt mixture surface. As the binder content of a given asphalt mixture decreases, the amount of reflected light increases proportionally (as seen in curve shown in FIG. 7). The ACT is sensitive enough to measure the changes in reflected light. A major benefit of this method is the asphalt mixture can be measured immediately after mixing either in the laboratory or in an asphalt plant without requiring solvents or an ignition oven.

ACT Sample Preparation Procedure

Summary

1) Procedure to test an adhesion sample
   a) Boil a sample for 10 minutes in distilled water
   b) Dry the sample using a heat source
      i) 5 minutes under forced-draft heat source
      ii) Stir mixture to redistribute moisture
      iii) Repeat 2 times for total of 15 minutes drying
2) Preparing Sample
   a) Preparing Loose Sample
      i) Use circular pan
      ii) Pour in mixture and stir
      iii) Press the surface flush
   b) Preparing Compacted sample
      i) Use an open ended mold
      ii) Pour the mixture into the mold placed on a hard surface
      iii) Using a ram in the shape of the mold, gently press down on the sample
      iv) The advantage of compacting the sample is that it provides the capability of measuring both surfaces of the sample, in case mixture segregation occurs during pouring of the sample into the measurement pan or mold.

Detailed Summary

Drying Procedure

1. Drain water from container used to boil the asphalt mixture.
2. Pour the wet boiled asphalt mixture into a flat-bottomed container.
3. Spread the mixture as thinly as possible at one end of the container. Elevate this end of the container to drain any remaining water in the loose mixture. The excess water can be removed using a rag or a force-draft heat source.
4. Place a forced-draft heat source in the testing stand at a certain height from the surface.
5. Direct the heat source at the mixture in the container for 5 minutes. An electrical timer can be used to turn off the heat source.
6. After 5 minutes, stir the loose mixture with the spatula to redistribute the damp mixture.
7. Repeat steps 4 and 5 two more times for a total drying time of 15 minutes.

Sample Preparation

1. Pour mixture into the testing container.
2. For measurement of loose mixtures, stir the mixture three complete revolutions using a spoon or similar device. For each stir, insert the spoon into the mixture until the spoon touches the bottom of the pan. Then, in a continuous circular motion, fold (i.e., scoop and lift) the fines into the coarse aggregates at the bottom of the pan.
3. Smooth out the surface of the mixture with the spoon.
4. Use a flat-bottomed container (tamper) to compress the mixture to a constant thickness. The mixture can be compressed by rotating and pressing or dropping the tamper.
5. For measurement of compacted mixtures, pour the dry sample into an open ended mold. Using the tamper, lightly press the top surface of the sample to compact or mold the sample into a puck, in the case of a cylindrical mold. The sample can be compacted into other mold shapes of appropriate size and accommodating gradation dependent stripping properties to be measured by the system.

Figure 1:
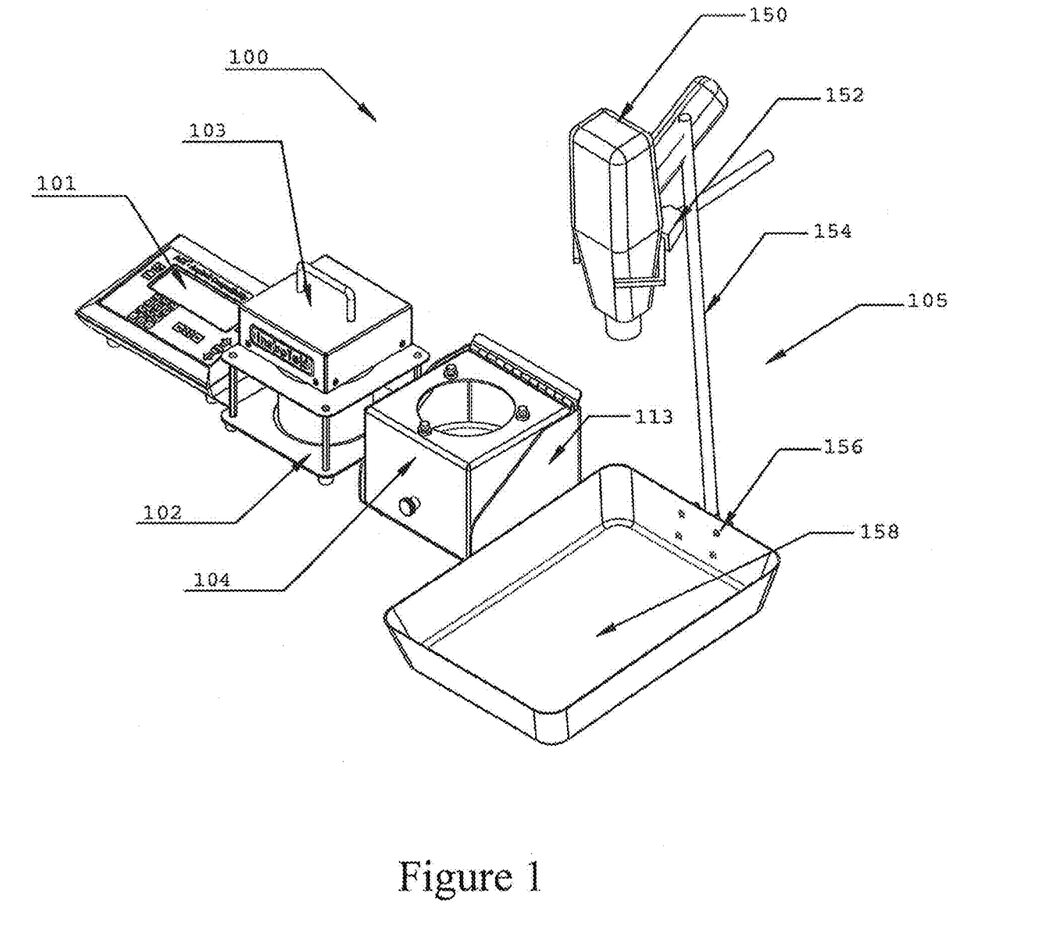
FIG. 1 is a perspective view of an Asphalt Compatibility or Quality Tester (ACT) system or kit according to some embodiments of the present invention.
Figure 2:
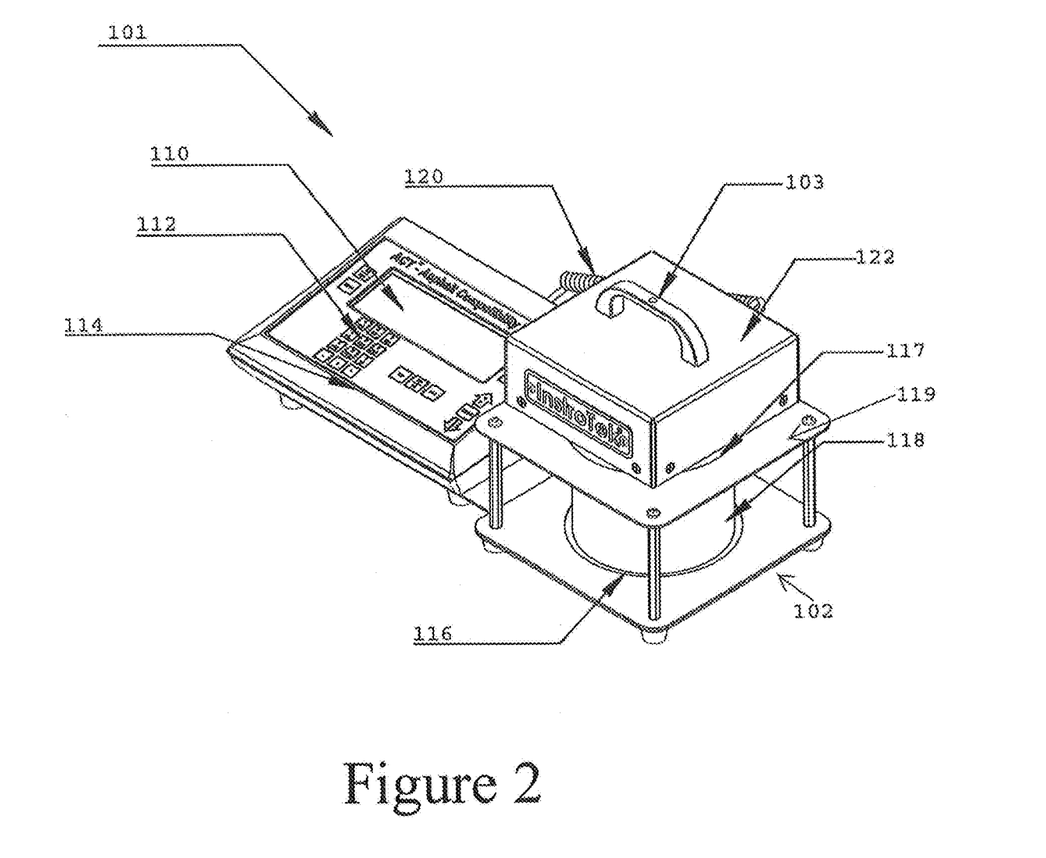
FIG. 2 is a perspective view of an ACT controller, sensor, and standard holder of the system of FIG. 1.

FIG. 1 shows an embodiment of the asphalt compatibility or quality tester (ACT) device or system 100 set up to evaluate the compatibility of an asphalt mixture after it has been boiled in water for 10 minutes. This device includes several components: an electronic controller 101, a standard holder 102, a measurement sensor 103, a testing cabinet 104, a sample preparation kit 200 or 200A (FIG. 4A or FIG. 4B), and a sample drying kit 105. Details of the electronic controller 101 and standard holder 102 are shown in FIG. 2. A cross-sectional view of the testing cabinet 104 and the measurement sensor 103 is shown in FIG. 3.

In FIG. 2, the electronic controller 101 may include a display such as an LCD display 110, a keypad 112, control electronics cabinet or housing 114, and internal electronic components. The electronic controller 101 allows the user to acquire the data, store the calibrations, and review the data. The standard holder 102 contains a reference material that is used as a standard 116 to normalize the effects of temperature, which is one of the benefits of the invention. The standard holder 102 has an opening 117 in the top plate or upper surface 119 of the holder to center a light tube 118 of the measurement sensor 103 over the standard 116. The standard holder 102 also can serve as a stand to hold the measurement sensor 103 when the sensor is not used to prevent damage to the standard 116 and the measurement sensor 103. The electronic controller 101 may be connected to the measurement sensor 103 using a cable 120. Those skilled in the art will immediately observe that the communication between the electronic controller 101 and the measurement sensor 103 may occur through various medium, such as Bluetooth, infrared, or different types of cable configuration and protocols.

Figure 3:
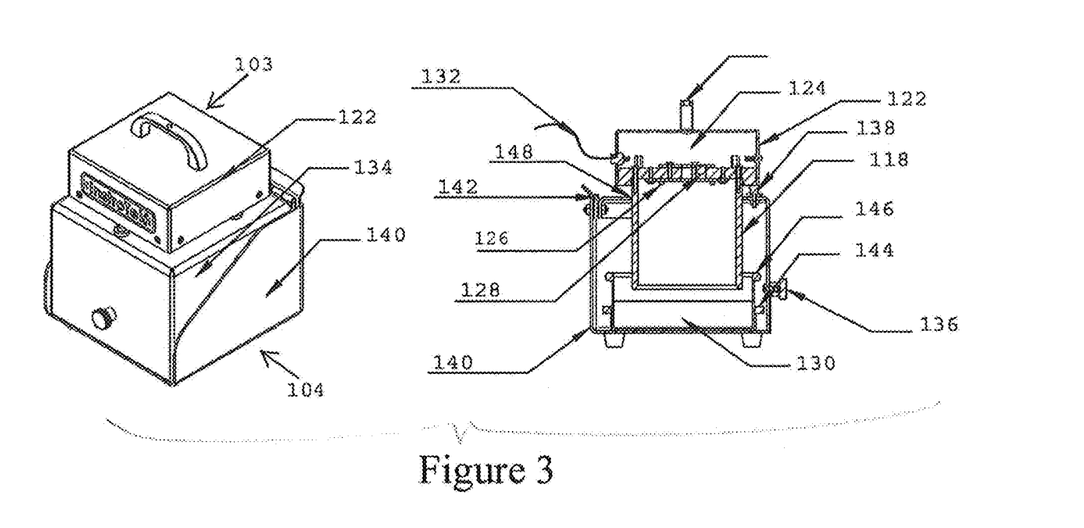
FIG. 3 includes a perspective view and a sectional view illustrating an ACT sensor positioned to measure sample in a testing cabinet of the system of FIG. 1.

FIG. 3 provides more details of the measurement sensor 103 and the testing cabinet 104. The measurement sensor 103 includes a sensor housing 122 which houses sensor electronics 124, light source 126 such as one or more LEDs, and light sensor 128. The light source 126 shines light along the light tube 118. The light is then reflected and refracted by the surface of the sample 130 and the light tube 118. The light that is reflected back toward the light source 126 is measured by the light sensor 128. The electronics 124 then convert the light sensor output to an analog or digital output that the controller 101 can convert to an engineering unit, such as % Loss. The sensor electronics 124 may be connected to the electronic controller 101 through a cable 132 (which may be the same as the cable 120) to allow operation of the measure electronics and acquire the response. Alternatively, the controller 101 and the measurement sensor 103 may communicate by an alternate means such as wirelessly.

The testing cabinet 104 includes an inner cabinet door 134 with a door knob 136 and standoffs 138 attached to it and an outer cabinet shell 140. The inner cabinet door 134 and outer cabinet shell 140 are connected by a hinge 142. Inside the testing cabinet 104 is a centering plate 144 to center a sample container 146 with the light tube 118. The testing cabinet has a light tube access hole or opening 148 in the top inner cabinet door 134 (or upper surface or top plate of the cabinet) to center the light tube 118 of the measurement sensor 103 over the sample container 146. The testing cabinet includes the standoffs 138 around the light tube access 148 to allow the sensor to sit a consistent distance above the surface of the sample to improve the repeatability of the results. The testing cabinet has the knob 136 and a hinge 142 on the inner cabinet door to allow easy access to the inside of the testing cabinet 104 to insert and remove the sample container 146 with different samples prepared using the sample preparation kit 200. Those experienced in the art would recognize that other possibilities for the testing cabinet 104 could include a cabinet with a drawer or a stand with a light tube access. In addition those skilled in the art would recognize that the measurement need not be stationary, e.g., the sample could be placed in the pan or sample container that rotates under the measurement sensor 103 either in steps or continuously. For example, the sample container 146 may be rotatable in the testing cabinet 104 (e.g., by a motor and/or a turntable). This would serve to obtain a good statistical average over the sample and reduce the error.

In some embodiments, the testing cabinet 104 may be omitted and the measurement sensor 103 may be placed on the sample surface or directly on a road surface.

Another component of the device is the sample drying kit 105. Referring again to FIG. 1, the drying kit 105 includes a dryer 150, dryer clamp 152, dryer stand 154, stand clamp 156, and drying pan 158. The dryer 150 is held above the drying pan 158 by the dryer clamp 152, dryer stand 154, and stand clamp 156. The dryer stand 154 and stand clamp 156 also allow the dryer pan 158 to be raised on one side to allow water to drain from wet asphalt mixture to decrease the drying time. For example, the stand 154 and/or the stand clamp 156 may extend below a bottom surface of the drying pan 158 to tilt the drying pan.

Figure 4A:
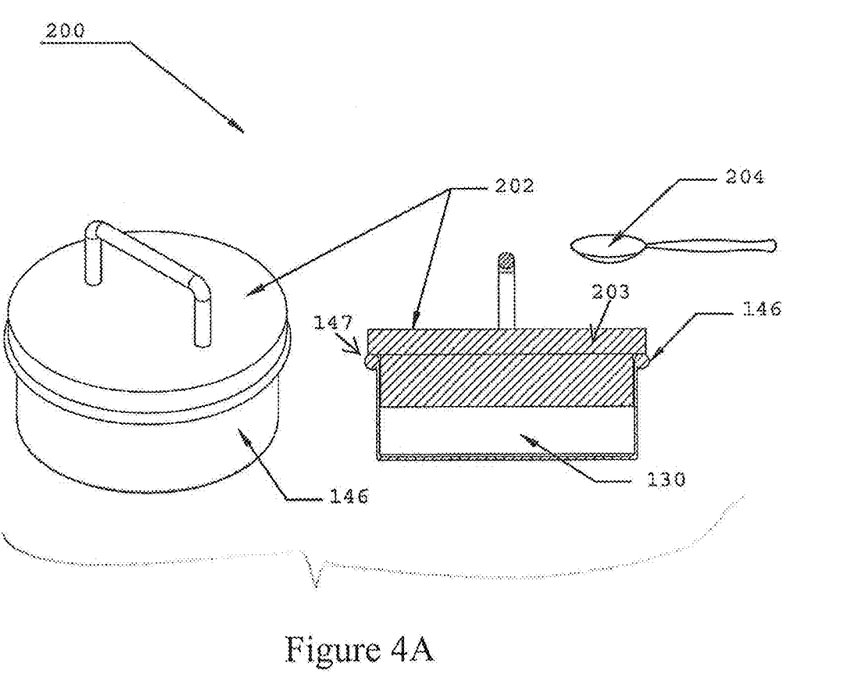
FIG. 4A is a sample preparation kit that can be used with the system of FIG. 1.

Referring to FIG. 4A, another component of the device is the sample preparation kit 200. The preparation kit 200 includes the sample container 146, a tamp 202, a stirring device 204, such as a spoon, and the dryer pan 158 (FIG. 1) to pour the material into the sample container 146. The asphalt mixture is poured into dryer pan 158. Then, the mixture is poured from the dryer pan 158 into the sample container 146. Then, the stirring device 204 is used to mix the coarse and fine particles in the sample container 146. Finally, the asphalt mixture sample is compressed using the tamp 202 to ensure a smooth, consistent surface to improve the consistency of the measurements. The distance, as seen in FIG. 3, between the sample 130 and the light source 126 and light sensors 128 is important and should be constant because the amount of reflected light decreases as the distance increases. Furthermore, a rough surface will reflect less light than a smooth surface. Stirring with the stirring device 204 and flattening the surface with the tamp 202 increase the consistency of the surface texture between samples of the same asphalt mixture. The tamp 202 may have a predetermined height and may include a flange 203 that engages an upper lip 147 of the sample container 146.

Figure 4B:
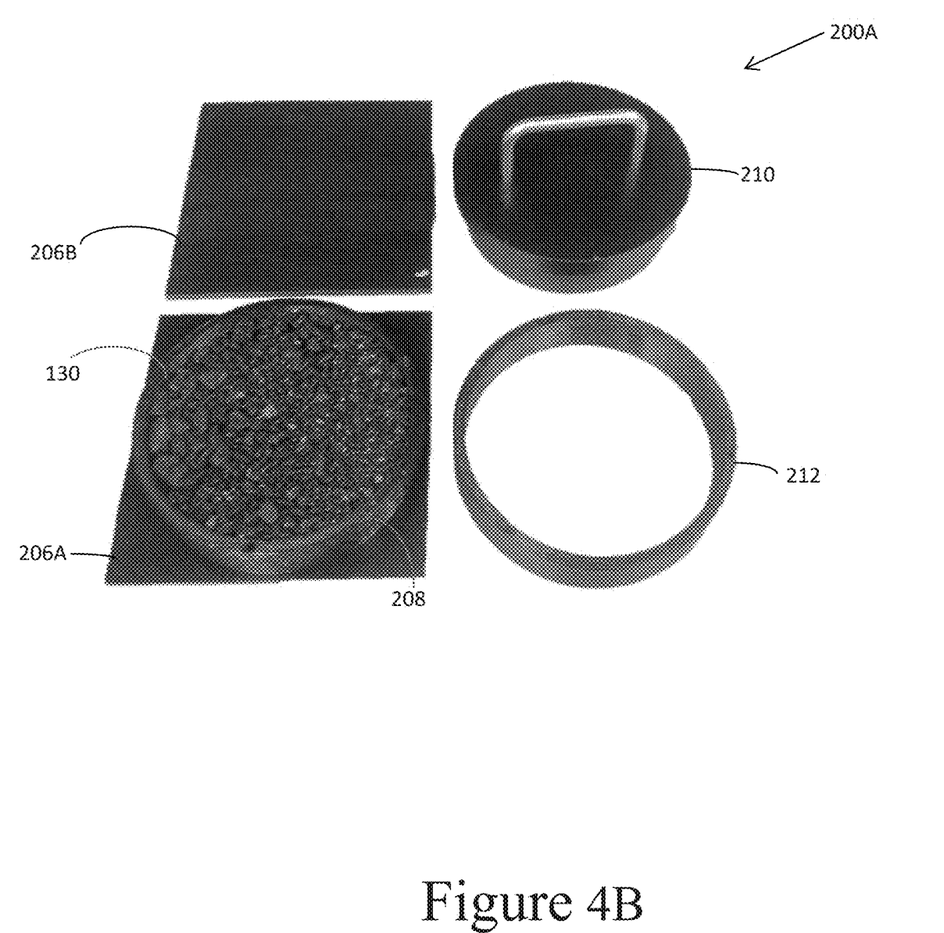
FIG. 4B is another sample preparation kit that can be used with the system of FIG. 1.

The sample preparation kit 200 may be used for loose mixture samples. Another sample preparation kit 200A that may be used for compacted mixture samples is illustrated in FIG. 4B. The kit 200A may include first and second plates 206A, 206B, an open ended mold 208, a tamp 210 (which may be the same or similar to the tamp 202 described above), and a mold extension 212. The loose asphalt mixture may be poured into the mold 208 that is placed on a hard surface such as one of the plates 206A, 206B. The loose mixture may be stirred to properly mix the sample. The mold extension 212 may be stacked on the mold 208. The asphalt mixture may be compacted using the tamp 210 to produce the compacted asphalt mixture sample 130. The mold extension 212 maybe removed and the sample 130, the mold 208, and/or the plate 206A may be placed in the testing cabinet 104 and measured as described herein. The sample 130 may be removed from the testing cabinet and flipped (e.g., onto the other plate 206B). The sample 130, the mold 208, and/or the plate 206B may be placed in the testing cabinet 104 and again measured as described herein. In this way, both sides or surfaces of the sample 130 are measured, and the compatibility of the sample can be based on the surface that indicates the worse % loss or some combination of the measurements collected from both surfaces of the sample 130 Alternatively all the measurements of both surfaces can be made directly outside of the testing cabinet 104, by placing the measurement sensor 103 directly on each surface of the sample 130 and following the compaction and flipping of the sample 130, as described above.

FIG. 5 shows an example of the data 300 acquired from the measurement sensor 103 by the electronic controller 101. The data 300 shows a relationship exists between the vertical axis defined as the engineering unit of % Loss 302 and the horizontal axis of the measurement sensor output defined as counts 304. The relationship is represented by a line 306 that represents the calibration. The calibration is determined by two points: the measured count for the unboiled mixture 308 and the measured count for the aggregates used in the asphalt mixture before mixing 310. These two values can be measured without boiling a sample 130 to determine an index for the amount of % Loss of adhesion. The verification data 312 show that the calibration is effective at predicting the % Loss.

Figure 6:
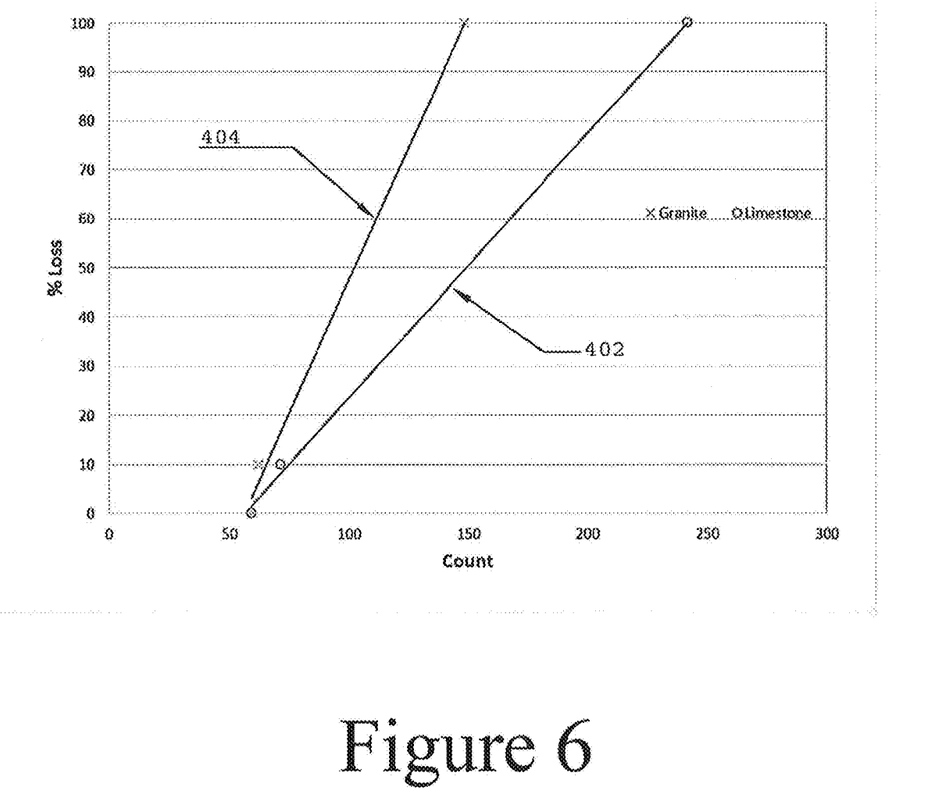
FIG. 6 is a graph illustrating calibration curves for different types of aggregate.

Aggregates from different sources can have different colors, so mixtures with different aggregates can have different calibration curves, as seen by comparing the two lines (402 and 404) in FIG. 6. At 150 counts, the ACT will read 50% loss for the limestone, while it will read 100% loss for the granite. For the slopes shown in FIG. 6, the normal range of readings will be 0-10%, which is less than the desired range of 0-35% normally seen with asphalt mixtures. The two aggregates were sprayed with water to obtain 040% loss for an average curve, which covers the desired range. This method of applying a color modifier is a novel way to account for color differences between bare aggregates and aggregates that have been stripped of its asphalt. A factory calibration that incorporates the variability in aggregate color can be developed to provide a % loss prediction for an average boiled asphalt mixture. If greater accuracy is desired, a mixture-specific calibration can be developed based on the following procedure.

Mixture Specific Calibration Procedure

The following procedure has been developed to calibrate the ACT to predict the % Loss for different aggregates.
1. Measure the count of the unboiled asphalt mixture. This value is 0% stripping.
2. Measure the count of the aggregate. The aggregate can be dry virgin, or coated with a color modifier, such as water, paint, epoxy, polyurethane, etc., depending on the application such as boil test or surface texture measurement, to more effectively represent the color of the aggregate after binder has been removed through mechanical and/or chemical wear. This value is 100% stripping.
   a. If applicable, apply the color modifier.
   b. Measure the count.
3. Determine the slope and intercept for % Loss vs. count.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

The invention claimed is:

1. A method for quality testing asphalt comprising:
   directing light from a light source to at least one surface of asphalt;
   detecting light reflected or refracted from the at least one surface of the asphalt using a light detector; and
   assigning a number indicating the quality of the asphalt in response to detecting light reflected or refracted from the at least one surface of the asphalt,
   wherein the asphalt is an asphalt sample, the method further comprising:
   providing an asphalt quality system comprising a measurement sensor comprising the light source and the light detector and a controller in communication with the measurement sensor,
   wherein assigning a number indicating the quality of the asphalt comprises, using the controller, determining a color index of the asphalt sample in response to detecting light reflected or refracted from the at least one surface of the asphalt sample,
   the method further comprising:
   using the controller, determining a binder loss value of the asphalt sample based on the determined color index; and
   using the controller, predicting an indirect tensile strength ratio (TSR) of the asphalt sample based on the binder loss value.

2. The method of claim 1 further comprising:
   preparing the asphalt sample; and
   receiving the asphalt sample in a sample container or open ended mold.

3. The method of claim 2 further comprising:
   displaying the color index of the asphalt sample and/or the binder loss value of the asphalt sample on a display of the controller.

4. The method of claim 2 wherein the asphalt quality system further comprises a testing cabinet, the method further comprising, before directing light from the light source to the at least one surface of the asphalt sample:
   loading the sample container or open ended mold with the asphalt sample therein in the testing chamber; and
   receiving the measurement sensor in the testing chamber.

5. The method of claim 4 wherein receiving the asphalt sample in a sample container or open ended mold comprises receiving the asphalt sample in a sample container, wherein the measurement sensor comprises a sensor housing holding a light source and a light detector and a light tube extending away from the sensor housing, and wherein receiving the measurement sensor in the testing cabinet comprises receiving at least a portion of the light tube in the sample container.

6. The method of claim 2 wherein preparing the asphalt sample comprises boiling the asphalt sample and drying the boiled asphalt sample.

7. The method of claim 6 wherein the asphalt quality system further comprises a drying kit comprising a dryer, a drying pan, and a drying stand and/or a stand clamp coupling the dryer and the drying pan, and wherein drying the boiled asphalt sample comprises:
   receiving the boiled asphalt sample in the drying pan;
   blowing air on the boiled asphalt sample using the dryer; and
   optionally tilting the drying pan such that water drains away from the boiled asphalt sample.

8. The method of claim 2 further comprising:
   using the asphalt quality system, determining a color index of an unboiled asphalt sample;
   using the asphalt quality system, determining a color index of a raw aggregate; and
   using the controller, determining a calibration curve based on the color index of the unboiled asphalt sample and the color index of the raw aggregate,
   wherein determining the color index of the asphalt sample comprises using the calibration curve.

9. The method of claim 2 wherein the asphalt quality system further comprises a standard holder configured to hold a standard comprising a reference material, the method further comprising:
   receiving the measurement sensor in the standard holder;
   directing light from the light source to the standard;
   detecting reflected light from the standard using the light detector; and
   using the controller, normalizing the effect of normal temperature changes in the laboratory to the sample by incorporating the response to detecting reflected light from the standard.

10. The method of claim 2 wherein receiving the asphalt sample in a sample container or open ended mold comprises receiving the asphalt sample in a sample container, the method further comprising tamping the asphalt sample in the sample container such that the asphalt sample is at a predetermined height in the sample container.

11. The method of claim 2, wherein receiving the asphalt sample in a sample container or open ended mold comprises receiving the asphalt sample in an open ended mold, wherein the at least one surface of the asphalt sample is a first surface of the asphalt sample, and wherein the color index is a first color index, the method further comprising:
    flipping the asphalt sample;
    directing light from the light source to a second surface of the asphalt sample that is opposite the first surface of the asphalt sample;
    detecting light reflected from the second surface of the asphalt sample using the light detector;
    using the controller, determining a second color index of the asphalt sample in response to detecting light reflected from the second surface of the asphalt sample; and
    optionally, using the controller, comparing the first and second color indexes of the asphalt sample.

12. The method of claim 11 wherein the asphalt quality system further comprises a testing cabinet, the method further comprising:
    removing the open ended mold with the asphalt sample therein from the testing cabinet before flipping the asphalt sample; and
    loading the open ended mold with the asphalt sample therein in the testing cabinet after flipping the asphalt sample.

13. An asphalt quality testing system comprising:
    a measurement sensor comprising a sensor housing holding a light source and a light detector and a light tube extending away from the sensor housing; and a controller in communication with the measurement sensor, wherein the controller is configured to determine a color index of an asphalt sample based on measurements of asphalt from the measurement sensor, wherein the controller is configured to output a binder loss index value based on the determined color index, wherein the controller is configured to predict an indirect tensile strength ratio (TSR) of the asphalt based on the determined binder loss index value.

14. The system of claim 13 wherein the measurement sensor is configured to direct light to a textured surface of the asphalt sample a plurality of times at different heights and positions and to detect reflected and/or refracted light from the textured surface to generate the measurements of the asphalt sample.

* * * * *

UNITED STATES PATENT AND TRADEMARK OFFICE
CERTIFICATE OF CORRECTION

PATENT NO. : 11,009,450 B2
APPLICATION NO. : 16/729617
DATED : May 18, 2021
INVENTOR(S) : LaCroix et al.

Page 1 of 1

It is certified that error appears in the above-identified patent and that said Letters Patent is hereby corrected as shown below:

In the Specification

Column 12, Line 38: delete "040%" and insert -- 0-40% --

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*